United States Patent [19]

Roizman et al.

[11] Patent Number: 5,334,498
[45] Date of Patent: Aug. 2, 1994

[54] HERPES SIMPLEX VIRUS 1 UL13 GENE PRODUCT: METHODS AND COMPOSITIONS

[75] Inventors: Bernard Roizman; Frances C. Purves, both of Chicago, Ill.

[73] Assignee: Arch Development Corporation, University of Chicago

[21] Appl. No.: 931,631

[22] Filed: Aug. 18, 1992

[51] Int. Cl.$^5$ ............................................. C12Q 1/70
[52] U.S. Cl. ..................................... 435/5; 435/183; 435/188; 435/194
[58] Field of Search .................... 435/5, 183, 188, 194

[56] References Cited

PUBLICATIONS

Ackermann, M., et al., J. Virol. (1984) 52:108–118.
Ackermann, M., et al., J. Virol. (1985) 56:207–215.
Baer, R., et al., Nature (London, 1984) 310:207–211.
Banks, et al., J. Gen. Virol. (1985) 66:1–14.
Barker, D. E. & Roizman, B., J. Virol. (1983) 66:562–566.
Batterson, W., et al., J. Virol. (1983) 45:397–407.
Batterson, W., et al., J. Virol. (1983) 46:371–377.
Chee, et al., J. Gen. Virol. (1989) 70:1151–1160.
Chou, J. & Roizman, B., J. Virol. (1986) 57:629–637.
Cunningham, C., et al., J. Gen. Virol. (1992) 73:303–311.
Davison, A. J. & Scott, J. E., J. Gen. Virol. (1986) 67:1759–1816.
Frame, et al., J. Gen. Virol. (1987) 68:2699–2704.
Honess, R. W. & Roizman, B., J. Virol. (1974) 14:8–19.
Lawrence, G. L., et al., J. Virol. (1990) 64:287–299.
Liu, F. & Roizman, B., J. Virol. (1991) 65:206–212.
Longnecker, R. & Roizman, B., Science (1987) 236:573–576.
Marsden, H. S., et al., J. Virol. (1978) 28:624–642.
McGeoch, D. J., et al., J. Mol. Biol. (1985) 181:1–13.
McGeoch, D. J., et al., J. Gen. Virol. (1988) 69:1531–1574.
McGeoch, D. J. & Davison, A. J., Nucl. Acids Res. (1986) 14:1765–77.
Post, L. E., et al., Cell (1981) 24:555–565.
Post, L. E. & Roizman, B., Cell (1981) 25:227–232.
Pereira, L., et al., Virology (1977) 77:733–749.
Purves, F. C., et al., J. Gen. Virol. (1986) 67:1049–1057.
Purves, F. C., et al., J. Virol. (1987) 61:2896–2901.
Purves, F. C., et al., J. Virol. (1991) 65:5757–5764.
Purves, F. C., et al., Eur. J. Biochem. (1987) 167:507–512.
Purves, F. C., et al., J. Virol. (1992) 66: in press.
Roller, R. J. & Roizman, B., J. Virol. (1991) 65:5873–5879.
Sears, A. E., et al., J. Virol. (1985) 55:338–346.
Smith, R. F. & Smith, T. F., J. Virol. (1989) 63:451–455.
Southern, E. M., J. Mol. Biol. (1975) 98:503–517.
Walboomers, J. M. & Ter Schagget, J., Virology (1976) 74:256–258.
Weller, S. K., et al., J. Gen. Virol. (1990) 71:2941–2952.
Wilcox, K. W., et al., J. Virol. (1980) 33: 167–182.
Purves et al., the UL13 gene of herpes simplex virus 1 encodes the functions for posttranslational processing associated with phosphorylation of the regulatory protein $\alpha 22$.
Proc. Natl. Acad. Sci 89: 7310–7314, 1992.

*Primary Examiner*—Esther L. Kepplinger
*Assistant Examiner*—Donna C. Wortman
*Attorney, Agent, or Firm*—Arnold, White & Durkee

[57] ABSTRACT

The present invention provides the gene product of the herpes simplex virus $U_L13$ gene as being capable of phosphorylating other gene products of the herpes simplex virus. The herpes simplex virus $U_L13$ gene product is used in an assay to identify substances suspected of having anti-herpes simplex viral activity.

2 Claims, 7 Drawing Sheets

HERPES SIMPLEX VIRUS 1 UL13 GENE PRODUCT: METHODS AND COMPOSITIONS

The government may own certain rights in the present invention pursuant to National Cancer Institute Grant CA47451.

TECHNICAL FIELD OF THE INVENTION

The present invention relates to the gene product of a herpes simplex virus $U_L13$ gene and the use of that gene product in an assay for screening substances for their anti-herpes simplex viral activity.

BACKGROUND OF THE INVENTION

The herpes simplex virus 1 (HSV-1) genome encodes at least 76 genes (McGeoch, et al., 1985; Chou, et al., 1986; McGeoch, et at., 1988; Liu, et al, 1991; Barker, et at., 1992). Inasmuch as three of the genes are contained within repeated sequences, the genome encodes at least 73 polypeptides. The 76 genes comprise several groups designated as $\alpha$, $\beta$ and $\gamma$, whose expression is coordinately regulated and sequentially ordered in a cascade fashion (Honess, et al., 1974). For the past two decades, this laboratory has investigated the mechanisms by which HSV-1 regulates the expression and function of its genes. In the course of these studies, we demonstrated that (i) initiation of transcription of viral genes is induced by a structural component of the virion (Post, et at., 1981; Batterson, et at., 1983), (ii) regulatory proteins induced by this process are phosphorylated (Pereira, et at., 1977; Marsden, et al., 1978) and (iii) binding of these proteins to DNA is affected by phosphorylation (Wilcox, et at., 1980). Since protein kinases (PK) are known to affect the function of regulatory proteins, we sought to identify the substrates of viral PKs and clarify their function.

Both HSV-1 $U_S3$ and $U_L13$ gene products contain motifs common to known protein kinases (McGeoch, et at., 1985; McGeoch, et at., 1988; McGeoch, et at., 1986; Smith, et at., 1989). Definitive evidence of $U_S3$ PK activity emerged from the observations that (i) the novel enzyme activity detected in cells infected with wild type virus was absent from uninfected cells and cells infected with a mutant from which the $U_S3$ gene had been deleted (Purves, et al., 1986; Frame, et al., 1987), and (ii) antibody raised against a synthetic eight-amino acid C-terminal $U_S3$ oligopeptide reacted with purified preparations of the enzyme (Frame, et al., 1987). Recently, we demonstrated that the most prominent target of the $U_S3$ PK is an essential, non glycosylated membrane protein encoded by a highly conserved herpesvirus gene, $U_L34$ (Purves, et al., 1991; Purves, et al., 1992). In the absence of $U_S3$, the nonphosphorylated $U_L34$ protein associates with several phosphorylated proteins not demonstrable in cells infected with wild type virus. Concurrently, it was shown that the $U_S11$ protein may act as an antiterminator of transcription of $U_L34$ inasmuch as (i) significant amounts of a truncated $U_L34$ mRNA accumulate in cells infected with a $U_S11-$ virus and (ii) the $U_S11$ protein binds to $U_L34$ mRNA immediately 5' to the truncation (Roller, et al., 1991). Although the functions of the $U_L34$ protein remain unknown, the regulation of its synthesis and expression deduced from the activities of $U_S11$ and $U_S3$ protein attest to its role in the reproductive cycle of the virus. Very little is known about the targets of the $U_L13$ PK. To investigate the role of $U_L13$ in the processing of the $U_L34$ protein, we constructed viral mutants lacking either the $U_L13$ gene or both the $U_L13$ and $U_S3$ genes. We report that a substrate of $U_L13$ PK is the product of the regulatory gene, $\alpha22$.

BRIEF SUMMARY OF THE INVENTION

In one aspect the present invention relates to a process of identifying a substance for its anti-herpes simplex viral ability comprising the steps of:

a) preparing a model system of phosphorylating a substrate of the herpes simplex virus $U_L13$ gene product;

b) selecting a substance suspected of having anti-herpes simplex viral acivity; and c) testing for the ability of said substance to modulate phosphorylation of said substrate and thus anti-herpes simplex viral activity in said model system.

In a preferred embodiment, a substrate used in a process of the present invention is herpes simplex virus infected cell protein 0, herpes simplex virus infected cell protein 22, herpes simplex virus US11 gene product, herpes simplex virus UL26 gene product, herpes simplex virus UL26.5 gene product or herpes simplex virus UL47 gene product.

A model system of phosphorylating such a substrate preferably contains an effective catalytic amount of a herpes simplex virus $U_L13$ gene product.

In a preferred embodiment, such a model system is prepared by forming an admixture by reacting an effective catalytic amount of herpes simplex virus $U_L13$ gene product with an effective amount of a substrate whose phosphorylation is catalysed by said herpes simplex virus $U_L13$ gene product in a liquid medium containing a phosphate donor.

BRIEF DESCRIPTION OF THE DRAWINGS

In the drawings which form a portion of this specification:

FIG. 1 shows schematic representations of the DNA sequence arrangements of the HSV-1 genome of deletion mutants. The top line: the genome of HSV-1(F)$\Delta305$ from which approximately 500 bp of the thymidine kinase (tk) gene had been deleted (Post, et al., 1981). The rectangles represent the inverted repeats flanking the unique sequences (thin lines) of the long and short components. The location of the tk gene is marked (TK). Line 1, relevant restriction enzyme sites present in the $U_L12-14$ genes shown on line 4. Lines 2 and 3, the EcoRV P and BglII O fragments, respectively. Line 5, the 581 amino acid $U_l13$ gene with protein kinase motifs located between the BstEII and HindIII cleavage sites their position is represented by the shaded rectangle. Line 6, the $U_L13$ gene of R7350 and R7354 viruses. In these recombinants an $\alpha27$-tk chimetic gene from pRB3968 was inserted into the BstEII site of the 2691 bp EcoRV P fragment cloned in the SmaI site of pGEM3z in pRB256. The resulting plasmid pRB4435 was co-transfected with intact R7040 or HSV-1(F)$\Delta305$ DNAs into rabbit skin cells and tk+ progeny viruses were selected in 143TK− cells as described (Post, et at., 1981) and designated as R7350 and R7354, respectively (Table 1). Recombinant virus R7350 also harbors the deletion in the $U_S3$ gene described previously (Longnecker, et at., 1987) and shown in line 12. Line 7, schematic representation of the sequences extending from the HindIII site (amino acid 155) to the BstEII site (amino acid 412) deleted from the $U_L13$ gene. Line 8, the DNA arrangement of recombinant viruses R7352, R7357 and R7358 in which the $U_L13$ sequences disrupted by the insertion or which had been deleted were restored by marker rescue with the MscI-KpnI fragment. Thus, the 2223 bp KpnI-MscI fragment from pRB4004 containing the HSV-1 BglII O was excised and cloned into the EcoRV site of pGEM5z to yield plasmid pRB4437. The pRB4437 DNA was cleaved with HindIII and BstEII, blunt ended with T4 polymerase and religated to yield pRB4439. Recombinant R7351 and R7355 were constructed by co-transfection of R7350 or of R7054 viral DNA with plasmid pRB4439 followed by selection of tk⁻ progeny as described (Post, et at., 1981). Removal of the HindIII-BstEII fragment deleted 45% of the $U_L13$ codons (amino acid 155 to 412 including the predicted conserved PK motifs). Recombinants R7352, R7357, and R7358 were constructed by marker rescue of recombinant viruses R7351, R7350 and R7354, respectively. Plasmid pRB4437 was co-transfected with intact viral DNAs and the progeny were selected for tk⁻ (R7357 and R7358). The progeny of individual plaques were examined for the presence of an intact 5.2 Kbp BglII O fragment. Line 9, areas of the relevant BamHI fragments which contain the genes $U_S1$ ($\alpha$22), $U_S2$, $U_S3$ (PK), $U_S4$ (glycoprotein G), and $U_S5$, shown in line 10. Line 11, the 481 amino acid $U_S3$ gene with conserved protein kinase motifs represented by the shaded rectangle. Line 12, schematic representation of the $U_S3$ sequences spanning from the PstI site at amino acid 69 to the BamHI site at amino acid 357 deleted from R7040, R7041, R7350 and R7351 viruses. Line 13, representation of the region of R7306 in which the deleted $U_S3$ PK sequences of R7041 have been restored by marker rescue.

FIG. 2 shows autoradiographic images of BglII digests of recombinant viral DNAs. Vital DNAs were prepared from NaI gradients as previously described (Walboomers, et al., 1976), digested with BglII, electrophoretically separated on 0.8% agarose gels, transferred to nitrocellulose membranes, and hybridized with radiolabeled pRB4004, which contains the HSV-1(F) BglII O fragment. The band designated 5.2 Kbp represents the wild-type BglII 0 fragment present in recombinant viruses HSV-1(F)$\Delta$305 and R7040 ($\Delta U_S3$). The 6.7 kb band represents the BglII O fragment containing the $\alpha$27-tk gene in the $U_L13$ gene in recombinant viruses R7350 ($\Delta U_S3$, $U_L13i$) and R7354 ($U_L13i$). The 4.4kb bands detected in recombinant viruses R7351 ($\Delta U_S3$, $\Delta U_L13$) and R7355 ($\Delta U_L13$) represent the BglII O fragment of these viruses harboring a 773 bp deletion in the $\Delta U_L13$ gene.

FIG. 3 shows autoradiographic and photographic images of electrophoretically separated phosphoproteins from infected HEp-2 cell nuclei: Panel A represents $^{32}$P-labeled phosphoprotein profile of nuclear extracts of infected Hep-2 cells electrophoretically separated in denaturing 8.5% acrylamide gels, transferred to nitrocellulose and reacted with monoclonal antibody (Q1) to alkaline exonuclease as shown in panel B. The arrow indicates the 85,000 Mr alkaline exonuclease designated as ICP18. The faint, faster migrating species reacting with the antibody has been identified previously as a degradation product of alkaline exonuclease. To prepare nuclear extracts, infected labeled HEp-2 cell monolayers were washed with PBS-A and scraped into PBS-A and pelleted by centrifugation. The cells were disrupted with PBS-A containing 0.5% NP40 and the nuclei were pelleted by centrifugation, washed with PBS-A containing 0.1% NP40, extracted for 30 min at 4° C. in a buffer (50 mM Tris-HCl pH 7.5, 0.42M NaCl, 25% glycerol, 10% sucrose, 5 mM $MgCl_2$, 0.1 mM EDTA, 0.1% NP40, 0.1M KCl, 1 mM DTT, 1 mM PMSF), clarified by centrifugation and stored at −70° C. The procedures for electrophoretic separation in denaturing 8.5% or 10% polyacrylamide gels, electric transfer to nitrocellulose and staining with antibodies to specific HSV-1(F) proteins and or autoradiography were as previously described (Purves, et al., 1991; Purves, et al., 1992).

FIG. 4 shows autoradiographic images of electrophoretically $^{32}$P- and $^{35}$S-labeled lysates of infected BHK cells. The procedures for infection, radiolabeling and preparation of cell lysates were described elsewhere (Purves, et al., 1991; Purves, et al., 1992). Panel A: autoradiogram of $^{32}$P-labeled proteins separated in denaturing gels containing 10% acrylamide. The closed circle indicate the increased amounts of the 70 kd phosphoprotein observed in lysates of BHK cells infected with the $U_L13i$ or $\Delta U_L13$ viruses. The letters a–d indicate the four new phosphoproteins which are present in cells infected with $\Delta U_S3$ viruses. The solid square indicates the position of the UL34 protein. The molecular weight standards are indicated. Panel B: autoradiogram of $^{35}$S-methionine labeled proteins separated as described above. The positions of known ICPs are indicated.

FIG. 6 shows autoradiographic and photographic images of 32P-labeled nuclear extracts from infected HEp-2 cells. Panel A: autoradiogram of $^{32}$P-labeled nuclear extract proteins separated in denaturing gels containing 8.5% acrylamide. Panel B: photograph of the corresponding gel shown in panel A transferred to nitrocellulose and reacted with polyclonal antiserum R77 to ICP22. Panel C: lanes 16–22 represent a lower exposure of the same HEp-2 nuclear extracts of $^{32}$P-labeled proteins infected with the indicated viruses as shown in panel A. The preparation of labeled nuclear extract is described in the legend to FIG. 3. Nuclear extract proteins were separated in an 8.5% polyacrylamide gel. Lanes 23–27 show HEp-2 nuclear extracts which have been labeled with $\gamma^{32}$P-ATP in the presence of 1M NaCl in vitro. The five forms of ICP22 are indicated by the numbers 1–5. The positions of ICP18 (alkaline exonuclease; $M_r$85,000), ICP25 ($\alpha$TIF, $M_r$ 65,000), ICP27 ($M_r$ 63,000), and of UL34 ($M_r$ 30,000) protein represented by the square are indicated. The letters U, T, S, R, and Q in panel C identify the phosphoprotein of nuclear extracts of infected HEp-2 cells labeled with $\gamma^{32}$P-ATP in vitro. Approximately 2 $\mu$g of nuclear extract was suspended in 50 $\mu$l of kinase buffer containing 50 mM Tris HCl, 1M NaCl, 0.1% NP40, 50 mM KCl, 20 mM MgCl$_2$, 30 mM MgAc, 1 mM dithiothreitol, and 5 μCi of $\gamma^{32}$P-ATP and incubated at 37° C. for 20 rains. The reactions were terminated by denaturation with sodium dodecyl sulfate.

DETAILED DESCRIPTION OF THE INVENTION

The present invention provides a process of identifying a substance for its anti-herpes simplex viral ability. Such a process comprises the steps of:

a) preparing a model system of phosphorylating a substrate of the herpes simplex virus U$_L$13 gene product;

b) selecting a substance suspected of having anti-herpes simplex vital activity; and c) testing for the ability of said substance to modulate phosphorylation of said substrate and thus anti-herpes simplex viral acivity in said model system.

The expression product of herpes simplex virus gene U$_L$13 catalyses the transfer of a phosphate moiety from a phosphate donor to a substrate. That is, the U$_L$13 gene product functions as a protein kinase.

Substrates for the U$_L$13 gene product protein kinase include a number of proteins found in herpes simplex virus infected cells and protein products of particular herpes simplex gene expression. Exemplary and preferred infected cell protein (ICP) substrates are designated ICP0 and ICP22. ICP22 is a gene product of herpes simplex virus regulatory gene α22. ICP22 is also referred to herein as α22 protein.

Exemplary and preferred gene product substrates are the gene products of herpes simplex virus US11 gene, herpes simplex virus UL26 gene, herpes simplex virus UL26.5 gene or herpes simplex virus UL47 gene.

The herpes simplex virus UL26 gene product functions as a protease enzyme. Herpes simplex virus UL26.5 gene product is thought to be a substrate for that protease. The herpes simplex virus US11 gene product acts as an anti-terminating agent for transcription of the U$_L$34 gene.

At least some of the substrates of U$_L$13 gene product kinase activity play a role in viral replication and appear late in viral infection. Where infection occurs with a virus deficient in U$_L$13 gene product expression, viral replication is inhibited and those substrate molecules are altered (ICP22, the UL47 gene product) or substantially decreased in abundance (the US11, Ul26, UL26.5 gene products).

In accordance with those observations, a model system for studying phosphorylation of U$_L$13 gene product substrates preferably comprises an effective catalytic amount of a herpes simplex virus U$_L$13 gene product.

In a preferred embodiment, such a model system is prepared by forming an admixture by reacting an effective catalytic amount of herpes simplex virus U$_L$13 gene product with an effective amount of a substrate whose phosphorylation is catalysed by said herpes simplex virus U$_L$13 gene product in a liquid medium containing a phosphate donor.

Herpes simplex virus U$_L$13 gene product is preferably obtained from cells or organisms infected with the virus. Means for isolating and purifying products of viral gene expression in infected cells are well known in the art. A suitable substrate for use in a process of the present invention can also be obtained from infected cells.

The following examples illustrate particular embodiments of the present invention and are not limiting of the specification and claims in any way.

EXAMPLE 1

The herpes simplex virus 1 U$_L$13 gene encodes the functions for post-translational processing associated with phosphorylation of the regulatory protein α22.

Materials and Methods

Cells and Virus

All cell lines were from ATCC. The derivation of viruses used in this study were as described in Table 1.

TABLE 1

The phenotype and genotype of HSV-1 mutants used in this study.

| Virus | Genotype[a] | Phenotype |
| --- | --- | --- |
| HSV-1(F) | Wild type | TK$^+$, PK$_{US3}^+$, PK$_{UL13}^+$ |
| HSV-1(F)Δ305 | ΔU$_L$23/ΔU$_L$24 | TK$^-$, PK$_{US3}^+$, PK$_{UL13}^+$ |
| R7040 | ΔU$_L$23/ΔU$_L$24, ΔU$_S$3 | TK$^-$, PK$_{US3}^-$, PK$_{UL13}^+$ |
| R7041 | ΔU$_S$3 | TK$^+$, PK$_{US3}^-$, PK$_{UL13}^+$ |
| R7306 | U$_S$3(R) | TK$^+$, PK$_{US3}^+$, PK$_{UL13}^+$ |
| R7350 | ΔU$_L$23/ΔU$_L$24, ΔU$_S$3, U$_L$13i | TK$^+$, PK$_{US3}^-$, PK$^{UL13-}$ |
| R7351 | ΔU$_L$23/ΔU$_L$24, ΔU$_S$3, U$_L$13 | TK$^-$, PK$_{US3}^-$, PK$_{UL13}^-$ |
| R7352 | ΔU$_L$23/ΔU$_L$24, ΔU$_S$3, U$_L$13(R) | TK$^-$, PK$_{US3}^-$, PK$_{UL13}^+$ |
| R7354 | ΔU$_L$23/ΔU$_L$24, U$_L$13i | TK$^+$PK$_{US3}^+$, PK$_{UL13}^-$ |
| R7355 | ΔU$_L$23/ΔU$_L$24, ΔU$_L$13 | TK$^-$, PK$_{US3}^+$, PK$_{UL13}^-$ |
| R7357 | ΔU$_L$23, ΔU$_S$3, U$_L$13i(R) | TK$^-$, PK$_{US3}^-$, PK$_{UL13}^+$ |
| R7358 | ΔU$_L$23, U$_L$13i(R) | TK$^-$, PK$_{US3}^+$, PK$_{UL13}^+$ |
| R325 | Δα22 | α22$^-$ |

[a]Δ- gene contains deletion; i- gene mutagenized by the insertion of α27-tk gene; R- wild type sequences restored in the mutant.

Results

The U$_L$13 gene is non-essential in cell culture

Figure 1:
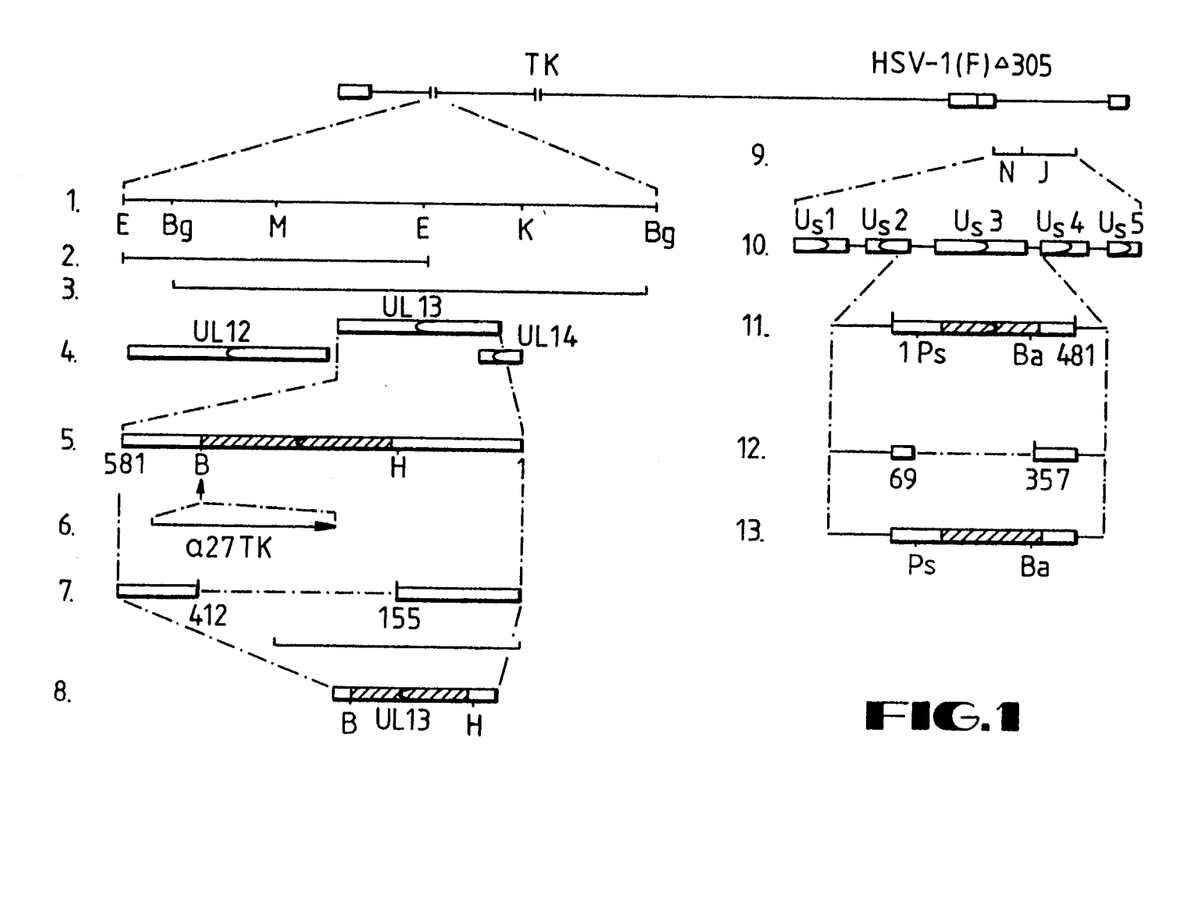
Figure 2:
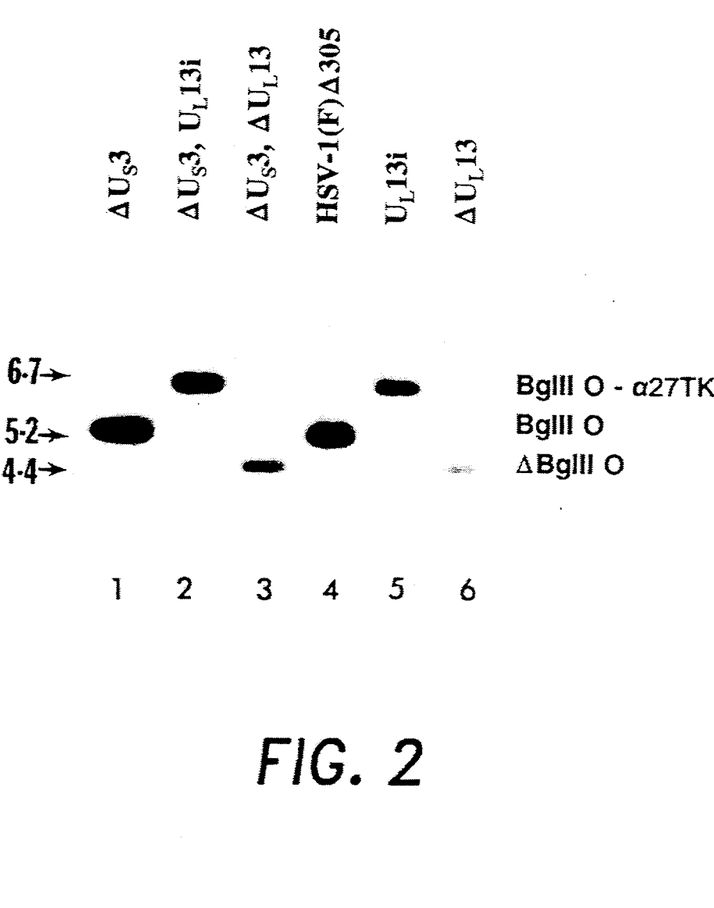
Figure 3A:
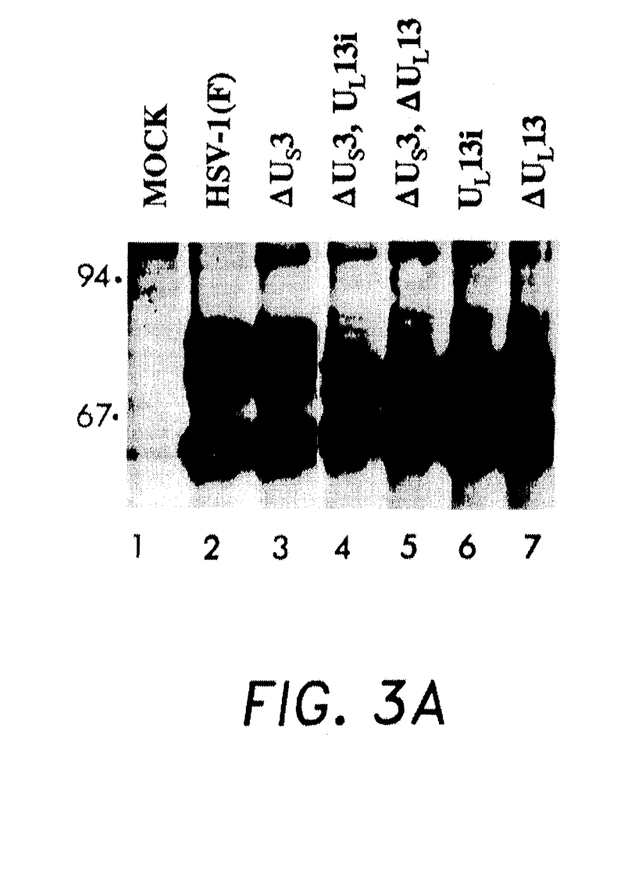
Figure 3B:
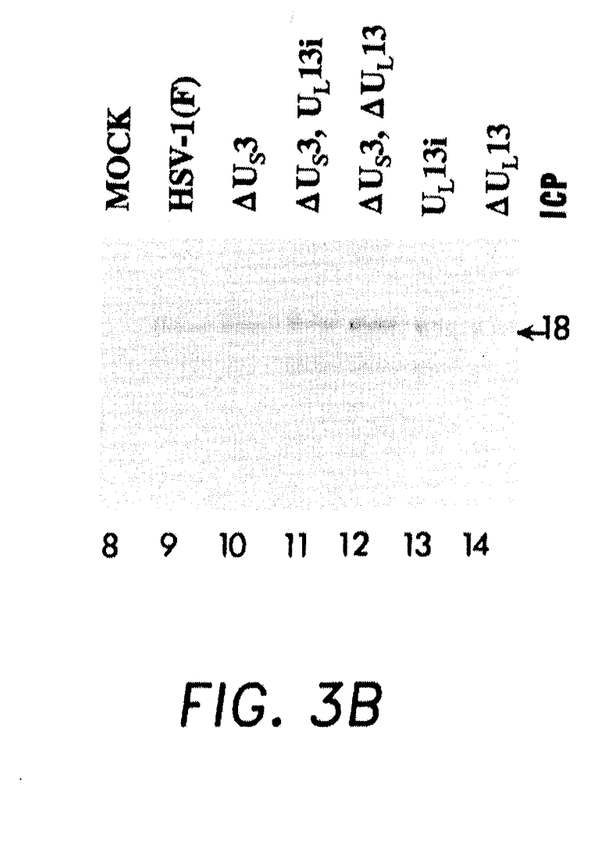

The construction and genotype of the recombinant viruses R7350, R7351, R7354, and R7355, detailed in FIG. 1 and its legend, follows the protocols described earlier (Post, et al., 1981), and involves the selection of recombinant viruses containing a chimeric α27-tk gene inserted in or near the target gene, followed by selection of the recombinant from which both the tk gene and the target sequences have been deleted. Verification of the structure of genetically engineered viruses was by Southern analysis (Southern, E. M., 1975) shown in FIG. 2. To guard against introduction of adventitious mutations, the assays included viruses designated with an (R) in which the deleted sequences were restored by marker rescue with a small fragment. All four recombinant viruses replicated on rabbit skin, 143TK$^-$, HEp-2, Vero, and BHK cells. During construction of the recombinant viruses, however, it was noted that viruses deleted in the U$_L$13 gene (ΔU$_L$13) yielded fewer plaques which were also of smaller size than those of the wild type virus, a property shared with mutants in the U$_L$12 gene encoding the alkaline exonuclease (Weller, et al., 1990). These properties are not due to a deletion or a decrease in the amount of the U$_L$12 gene product inasmuch as U$_L$13$^-$ mutants produced amounts of alkaline exonuclease comparable to those of wild type viruses (FIG. 3). The impairment in growth and plaque formation was due to the deletion or inactivation of the U$_L$13 gene inasmuch as the wild type phenotype was restored by marker rescue of the gene. We conclude that the U$_L$13 gene is non-essential in cell culture either in the presence or absence of the $U_S3$ gene, but that viral replication may be significantly impaired in some cell lines in the absence of the $U_L13$ protein.

Figure 4A:
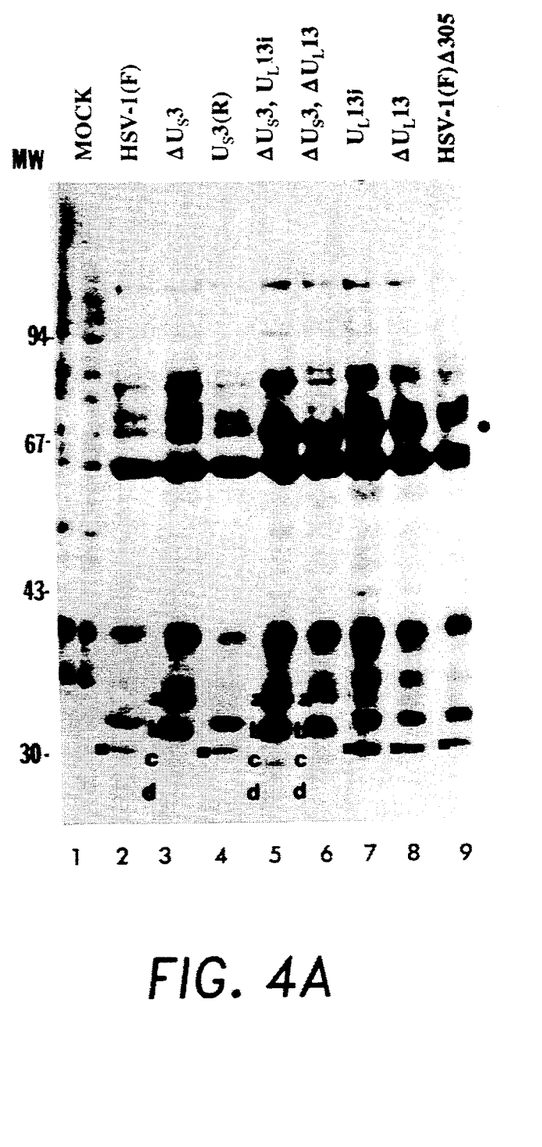
Figure 4B:
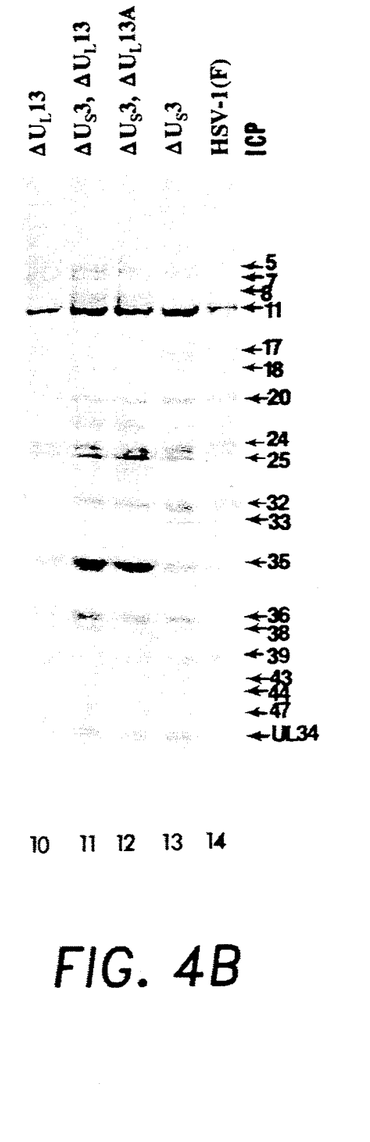

The novel phosphoproteins present in cells infected with the $\Delta US3$ viruses are not dependent upon the $U_L13$ gene product The four phosphoproteins (labeled a-d in FIG. 4) were shown elsewhere (Purves, et at., 1992) to be present and associated with $U_L34$ protein in $^{32}$P-labeled lysates of BHK cells infected with recombinant viruses in which either the $U_S3$ gene had been deleted or which contained site specific mutations in the PK target site of the $U_L34$ protein. In order to determine whether these proteins are phosphorylated by $U_L13$ but only when $U_L34$ protein is incompetent in turning $U_L13$ off, we examined the phosphoproteins in cells infected with both single mutants ($\Delta U_L13$) or double mutants ($\Delta U_L13$, $\Delta U_S3$). As illustrated in FIG. 4, lanes 3, 5, and 6, the tetrad (a, b, c, and d) of novel phosphoproteins was present in cells infected with all $\Delta U_S3$ viruses, regardless of whether the $U_L13$ gene was present, deleted ($\Delta U_L13$) or disrupted by insertion ($U_L13i$). These results do not support the hypothesis that $U_L13$ gene product is involved in the association of the novel phosphoproteins with the unphosphorylated form of $U_L34$ protein.

Figure 5A:
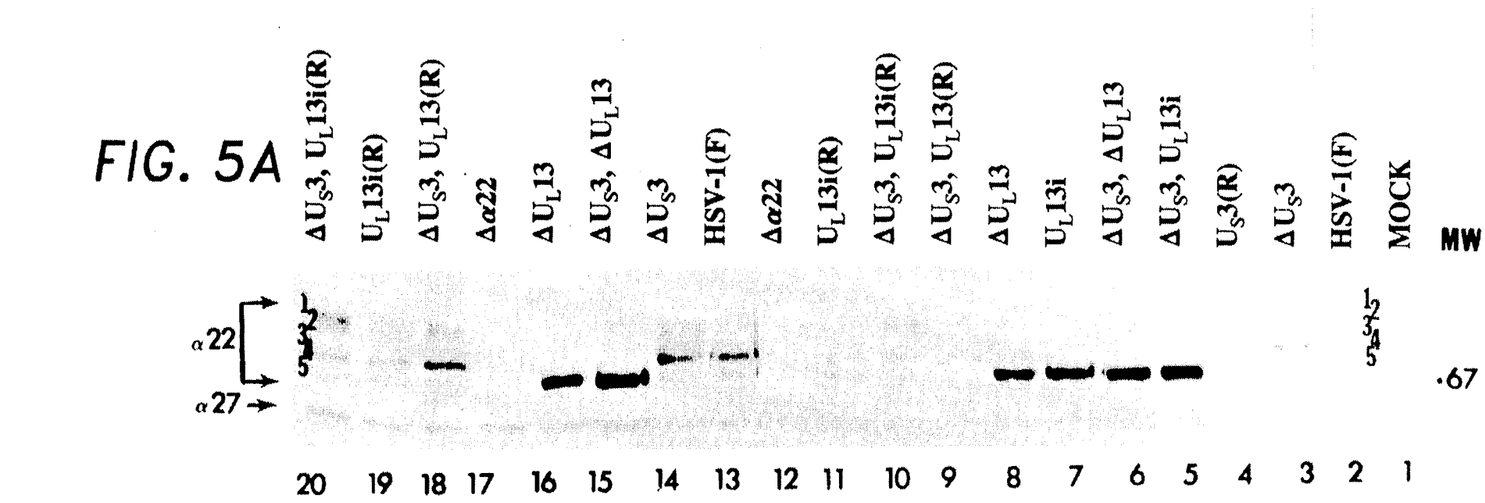
FIG. 5 shows photographic and autoradiographic images of electrophoretically separated $^{32}$P-labeled and $^{35}$S-methionine labeled lysates of infected cells. Panel A: photograph of proteins electrophoretically separated in 8.5% acrylamide denaturing gels, transferred to nitrocellulose and reacted first with a polyclonal R77 antiserum specific for ICP22, and then with monoclonal antibody H1117 to ICP27 as a control for equal infectivity. The five forms of ICP22 protein are indicated in lanes 2 and 20, and the position of ICP27 is indicated by the single arrow in panel A. Panel B, represents the corresponding autoradiogram, lanes 1–12 are separated infected cell proteins labeled with 32P and lanes 13–20 are separated infected cell proteins labeled with 35S-methionine. Known ICPs are indicated by arrows, and a $M_r$ 67,000 marker is included.
Figure 5B:
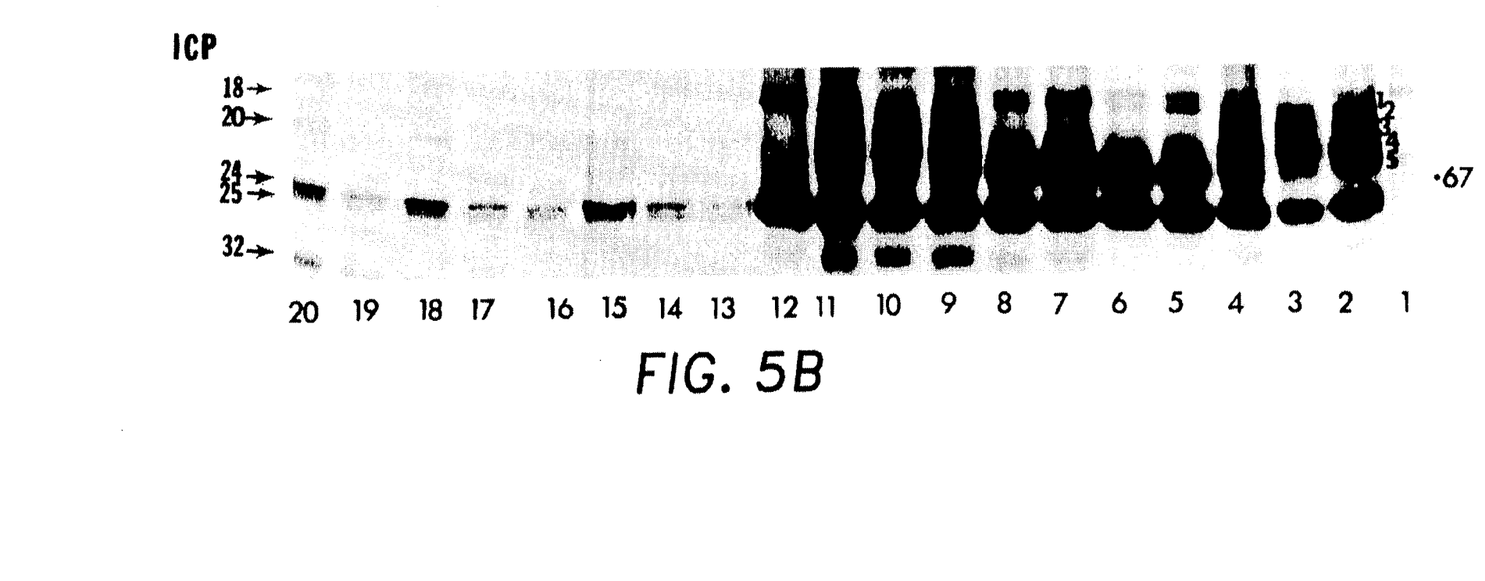
Figure 6A:
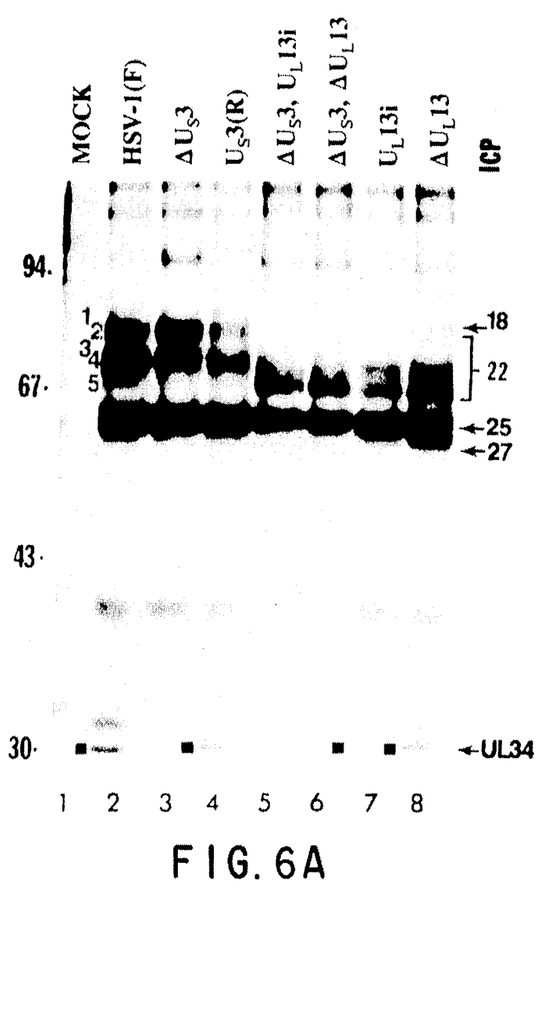
Figure 6B:
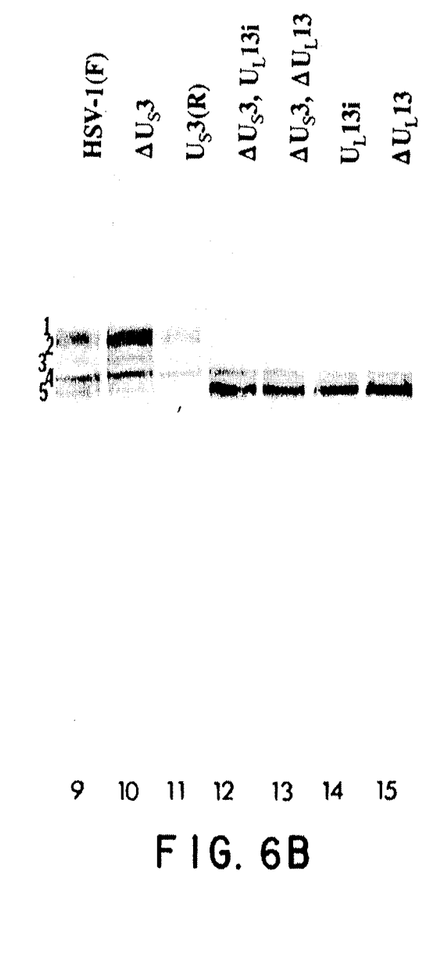
Figure 6C:
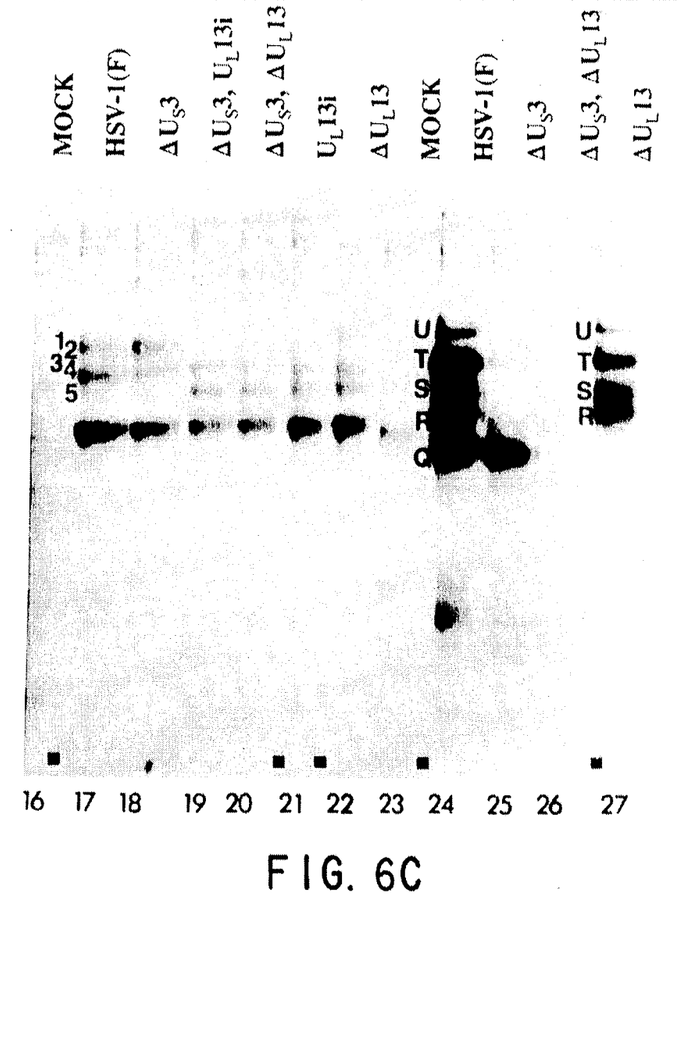

Disruption or deletion of the $U_L13$ open reading frame alters the post-translational modification of the $\alpha 22$ protein in vivo As shown in FIG. 4, panel A, lysates of BHK cells infected with $\Delta U_L13$ or $U_L13i$ viruses contained a prominent $^{32}$P-labeled band migrating with an apparent $M_r$ of 70,000 (indicated by the closed circle). The appearance of this band did not correlate with deletions in the $U_S3$ gene. Further studies of the lysates of BHK cells (FIG. 5, panel B, lanes 1–12) or of nuclear extracts of HEp-2 cells (FIG. 6, panel A, lanes 1–8) revealed five phosphoprotein species ranging in $M_r$ from 70,000 to 82,000 (identified in FIG. 5, lane 2, and FIG. 6, lane 2, by numbers 1–5) whose absence, presence and amount were consistently correlated to the state of the $U_L13$ gene. Specifically, in cell lysates or nuclear extracts of cells infected with $\Delta U_L13$ or $U_L13i$ recombinants, the $M_r$ 70,000 phosphoprotein (No. 5) appeared to be either hyperphosphorylated or present in increased amounts, whereas the higher $M_r$ phosphoproteins (No 1–3) appear to be either absent or hypophosphorylated (FIG. 5, panel B, lanes 5–8; FIG. 6, panel A, lanes 5–8). Inasmuch as restoration of the $U_L13$ sequences restored the wild type phenotype in both BHK cells (FIG. 5, panel B, lanes 9–11) and HEp-2 cells (data not shown) the observed phenotype reflected the $U_L13$ genotype.

To determine whether the phosphorylated proteins designated by the numbers 1–5 corresponded to known viral phosphoproteins, electrophoretically separated lysates of infected cells were electrically transferred to a nitrocellulose sheet and reacted with antibodies to ICP27 (H 1117), $\alpha$TIF (LP1), ICP22 (R77), and the alkaline exonuclease (Q1) (Ackermann, et al., 1984; Ackermann, et al., 1985; Banks, et al., 1985). The results (FIG. 5, panel A and FIG. 6, panel B) indicate that the phosphoproteins 1–5 comigrate with post-translationally modified forms of the ICP22. Conclusive evidence of the identity of these proteins is based on the absence of these bands in cells infected with R325 (FIG. 5 panels A and B, lane 12), a recombinant virus from which a portion of the $\alpha 22$ gene had been deleted (Post, et al., 1981). As a control for equal infectivity, the same immunoblot (FIG. 5 panel A) was also reacted with monoclonal antibody to the ICP27. In BHK cells infected with $U_L13^-$ virus, (FIG. 5, panel A, lanes 5–8, 15–16) most of the ICP22 was present as a $M_r$ 70,000 protein (No 5) and only a small amount comigrated with the No. 4 band. A similar pattern was seen in nuclear extracts of HEp-2 cells infected with $U_L13^-$ viruses (FIG. 6 panel B, compare lanes 9–11 with 12–15) except that traces of the higher molecular weight species (No. 2 and 3) were present. We conclude that the $U_L13$ gene product mediates post-translational processing which is associated with phosphorylation of ICP22 to the apparent higher molecular weight species (bands No. 1–4).

The phosphoprotein profiles of nuclear extracts obtained from HEp-2 cells infected with the $U_L13$ deletion viruses labeled with $\gamma^{32}$P-ATP in vitro differed significantly from those labeled with $^{32}P_i$ in vivo Nuclear extracts of HSV-1(F) infected cells labeled in vitro with $\gamma^{32}$P-ATP in the presence of 1M NaCl exhibited five labeled bands designated as U, T, S, R and Q (FIG. 6, Panel C, lane 24). Inasmuch as phosphoproteins U, T, S and R were absent from cells infected with $\Delta U_S3$ viruses (FIG. 6, panel C, lanes 25–26), they represent proteins whose phosphorylation is either directly or indirectly mediated by the $U_S3$ PK. Phosphoproteins S and R are likely to be the $U_S3$ PK itself, which forms a doublet and is known to autophosphorylate. Phosphoprotein U was identified as the alkaline exonuclease by its reactivity with the Q1 monoclonal antibody. Phosphoprotein T is presently under investigation. Phosphoprotein Q, however, which has an apparent $M_r$ of 57,000, is present only in cells infected with viruses encoding an intact $U_L13$ gene.

A recent report (Cunningham, et at., 1992) identified a kinase activity present in the nuclei of infected cells which phosphorylates a $M_r$ 57,000 protein. The activity maps between $U_L9$ and $U_L15$ genes and is immunoprecipitable with anti-$U_L13$ antisera. The authors suggested that the observed event may be $U_L13$ autophosphorylation. This interpretation is consistent with our results, but whether the actual kinase activity is $U_L13$ itself has not been established.

Discussion

The $U_L13$ protein, like the $U_S3$ PK, is non-essential for HSV-1 replication in cell culture, although viral yields appear to be diminished. The predicted sequence of the $U_L13$ protein contains amino acid motifs which are characteristic of the catalytic domains of eukaryotic PKs, and possibly bacterial phosphotransferases (Smith, et at., 1989; Chee, et at., 1989). By analogy with the $U_S3$ PK (Purves, et at., 1986; Purves, et al., 1987; Purves, et at., Eur. J. Biochem. 1987), determination of the enzymatic activity will require studies on purified protein. Whereas the $U_S3$ PK is mainly a cytoplasmic kinase (Purves, et al., 1986), the $U_L13$ protein is readily detected in the nucleus (Cunningham, et al., 1992). Whereas the major substrate of the $U_S3$ PK is the $U_L34$ membrane protein (Purves, et at., 1992), the prominent target of $U_L13$ is ICP22. Furthermore, whereas $U_S3$ is conserved only among the alphaherpesviruses (McGeoch, et al., 1986; Baer, et at., 1984; Davison, et at, 1986), the $U_L13$ gene is conserved among all three herpesvirus subfamilies (varicella zoster, (Davison, et at, 1986), human cytomegalovirus, (Chee, et at., 1989), human herpes virus 6, (Lawrence, et at., 1990) and Epstein Barr Virus, (Baer, et al., 1984).

The $M_r$ 70,000 species (No. 5) of ICP22 and trace amounts of higher mol. weight species (No. 2–4) predominate in extracts of cells infected with the $U_L13^-$ viruses. The stepwise increases in molecular weight between the five ICP22 subspecies are consistent with, but not indicative of, successive phosphorylations of the protein and appear to be cell type specific. The phosphorylation of the Mr. 70,000 species (No. 5) is independent of the $U_L13$ protein. Subsequent phosphorylation of ICP22 may represent direct phosphorylations by the $U_L13$ protein or by another infected cell PK activated by the $U_L13$ gene product. We note that ICP22 is predicted to have 45 serine and 28 threonine amino acids. The majority of these residues are flanked by clusters of acidic amino acids, particularly at the N-terminus between amino acid 38 and 118, and at the C-terminus between amino acids 296 and 385. The nuclear PK activity described by Cunningham et al. (Cunningham, et al., 1992) which phosphorylates the $U_L13$ protein also has a preference for acidic target sites of the type present in ICP22.

ICP22 has been implicated in the trans-activation of vital genes and as a protein involved in extending the host range of HSV-1 in cell culture (Sears, et al., 1985). In non permissive cells (e.g. rabbit skin, hamster, and rat cell lines) late protein synthesis was grossly reduced. ICP22 appears to exert a regulatory function which is complemented by cellular proteins in some cell lines. Since ICP22 is among the first viral proteins made after infection, it is conceivable that the $U_L13$ protein modifies ICP22 late in infection thereby altering its function. In this respect, the $U_L13$ gene may serve to regulate late gene expression via ICP22. It is noteworthy that $U_L13^-$ virus exhibited impaired growth on rabbit skin cells, and that in BHK cells infected with $U_L13^{31}$ virus, ICP22 was less extensively processed than in infected HEp-2 cells. The significance of the modifications of ICp22 are currently under study.

Further analyses of the protein profiles of cells infected with the $U_L13$ deletion viruses have related that the levels of specific viral late proteins are dramatically reduced in amount when compared to the levels observed in cells infected with either wild type virus or virus in which the $U_L13$ gene has been repaired. The proteins which are reduced include the products of $U_S11$, $U_L26$ (protease) and $U_L26.5$ (protease substrate), and three other viral proteins, two of which may correspond to the tegument proteins encoded by the $U_L47$ and $U_L49$ genes. This list of affected viral proteins cannot be considered as all inclusive, as many other viral protein levels have not yet been closely examined. It is noteworthy that not all late viral proteins appear reduced in cells infected with the $U_L13^-$ virus. Specifically, $\alpha$TIF and glycoprotein C proteins accumulate to wild type levels in the cells infected with the $U_L13$ deletion viruses, indicating that the modified ICP22 may target only certain viral genes.

Equally important, late genes do not appear to be the only kinetic class affected by the $U_L13$ mediated phosphorylation of ICP22. For example, while two $\alpha$ gene products, ICP4 and ICP27, accumulate to wild type levels in cells infected with either the ICP22 deletion of the $U_L13$ deletion viruses, the amounts of another $\alpha$ gene product ICP0 are significantly reduced to both. This observation is particularly significant, as ICP0 appears to play a critical role in several aspects of the viral life cycle. Numerous studies have implicated it as a promiscuous transactivator of viral gene expression during lytic replication. Recombinant viruses in which the $\alpha$0 gene has been deleted demonstrate impaired reactivation from latency.

In order to determine whether the reduced accumulation of proteins in the cells infected with the ICP22 and the $U_L13$ deletion viruses were due to reduced levels of mRNA in infected cells, the levels of mRNA encoding two of the affected proteins, ICP0 and $U_S11$, were measured by northern blot analysis. Both ICP0 and $U_S11$ mRNA levels were clearly decreased in cells infected with the mutant viruses, indicating either decreased transcription rates of these genes, or decreased stability of these mRNAs, in the absence of the $U_L13$ induced modification of ICP22.

References

The following references are incorporated herein by reference.

1. McGeoch, D. J., Dolan, A., Donald, S. & Rixon, F. J. (1985) J. Mol. Biol. 181, 1–13.
2. Chou, J. & Roizman, B. (1986) J. Virol. 57, 629–637.
3. McGeoch, D. J., Dalrymple, M. A., Davison, A. J., Dolan, A., Frame, M. C., McNab, D., Perry, L. J., Scott, J. E. & Taylor, P. (1988) J. Gen. Virol. 69, 1531–1574.
4. Liu, F. & Roizman, B. (1991) J. Virol. 65, 206–212.
5. Barker, D. E. & Roizman, B. (1992) J. Virol. 66, 562–566.
6. Honess, R. W. & Roizman, B. (1974) J. Virol. 14, 8–19.
7. Post, L. E., Mackem, S. & Roizman, B. (1981) Cell 24, 555–565.
8. Batterson, W., Furlong, D. & Roizman, B. (1983) J. Virol. 45, 397–407.
9. Batterson, W. & Roizman, B. (1983) J. Virol. 46, 371–377.
10. Pereira, L., Wolff, M., Fenwick, M. & Roizman, B. (1977) Virology 77, 733–749.
11. Marsden, H. S., Stow, N. D., Preston, V. G., Timbury, M. C. & Wilkie, N. M. (1978) J. Virol. 28, 624–642.
12. Wilcox, K. W., Kohn, A., Sklyanskaya, E. & Roizman, B. (1980) J. Virol. 33, 167–182.
13. McGeoch, D. J. & Davison, A. J. (1986) Nucleic Acids Res. 14, 1765–1777.
14. Smith, R. F. & Smith, T. F. (1989) J. Virol. 63, 451–455.
15. Purves, F. C., Katan, M., Stevely, W. S. & Leader, D. P. (1986) J. Gen. Virol. 67, 1049–1057.
16. Purves, F. C., Longnecker, R. M., & Roizman, B. (1987) J. Virol. 61, 2896–2901.
17. Frame, M. C., Purves, F. C., McGeoch, D. J., Marsden, H. S. & Leader, D. P. (1987) J. Gen. Virol. 68, 2699–2704.
18. Purves, F. C., Spector, D., & Roizman, B. (1991) J. Virol. 65 5757–5764.
19. Purves, F. C., Spector, D. & Roizman, B. (1992) J. Virol. 66, in press.
20. Roller, R. J. & Roizman, B. (1991) J. Virol. 65, 5873–5879.
21. Post, L. E. & Roizman, B. (1981) Cell 25, 227–232.
22. Southern, E. M. (1975) J. Mol. Biol. 98, 503–517.
23. Weller, S. K., Seghatoleslami, M. R., Shao, L., Rowse, D. & Carmichael, E. P. (1990) J. Gen. Virol. 71, 2941–2952.
24. Ackermann, M., Braun, D. K., Pereira, L. & Roizman, B. (1984) J. Virol. 52, 108–118.

25. Ackermann, M., Sarmiento, M. & Roizman, B. (1985) J. Virol. 56 207–215.
26. Banks, L., Purifoy, D. J. M., Hurst, P. F., Killington, R. A. & Powell, K. L. (1985) J. Gen. Virol. 66, 1–14.24.
27. Cunningham, C., Davison, A., Dolan, A., Frame, M. C., McGeoch, D. J., Meredith, D. M., Moss, H. W. M. & Orr, A. C. (1992) J. Gen. Virol. 73, 303–311.
28. Chee, M. S., Lawrence, G. L. & Barrell, B. G. (1989) J. Gen. Virol. 70, 1151–1160.
29. Purves, F. C., Katan, M. & Leader, D. P. (1987) Eur. J. Biochem. 167, 507–512.
30. Baer, R., Bankier, A. T., Biggin, M.D., Deininger, P. L., Farrell, P. J., Gibson, T. J., Hatfull, G., Hudson, G. S., Satchwell, S. C., Seguin, C., Turnell, P. S. & Barrell, B. G. (1984) Nature (London) 310, 207–211.
31. Davison, A. J. & Scott, J. E. (1986) J. Gen. Virol. 67, 1759–1816.
32. Lawrence, G. L., Chee, M., Craxton, M. A., Gompels, U. A., Honess, R. W. & Barrell, B. G. (1990) J. Virol. 64, 287–299.
33. Sears, A. E., Halliburton, I. W., Meignier, B., Silver, S. & Roizman, B. (1985) J. Virol. 55, 338–346.
34. Longnecker, R. & Roizman, B. (1987) Science 236, 573–576.
35. Walboomers, J. M. & Ter Schagget, J. (1976) Virology 74, 256–258.

What is claimed is:

1. A process of identifying a substance for its potential ability to impair herpes simplex vital replication comprising the steps of:
   a) forming an admixture of an effective catalytic amount of herpes simplex virus $U_L13$ gene product, and an effective amount of a substrate whose phosphorylation is catalyzed by said gene product in a liquid medium containing a phosphate donor;
   b) selecting a substance suspected of impairing herpes simplex viral replication; and
   c) testing for the ability of said substance to inhibit phosphorylation of said substrate and thus potentially to impair herpes simplex viral replication.

2. The process according to claim 1 wherein said substrate is infected cell protein 0, infected cell protein 22, herpes simplex virus US11 gene product, herpes simplex virus UL26 gene product, herpes simplex virus UL26.5 gene product or herpes simplex virus UL47 gene product.

* * * * *

UNITED STATES PATENT AND TRADEMARK OFFICE
CERTIFICATE OF CORRECTION

PATENT NO. : 5,334,498

DATED : August 2, 1994

INVENTOR(S) : Roizman et al.

It is certified that error appears in the above-identified patent and that said Letters Patent is hereby corrected as shown below:

In claim 1, column 12, line 7, delete "vital" and replace --viral-- therefor.

Signed and Sealed this

Eighth Day of November, 1994

Attest:

BRUCE LEHMAN

Attesting Officer     Commissioner of Patents and Trademarks